(12) United States Patent
Samproni

(10) Patent No.: US 11,850,585 B2
(45) Date of Patent: Dec. 26, 2023

(54) LOW SAMPLE VOLUME SENSING DEVICE

(71) Applicant: Siemens Healthcare Diagnostics Inc., Tarrytown, NY (US)

(72) Inventor: Jennifer A. Samproni, Braintree, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 638 days.

(21) Appl. No.: 17/035,919

(22) Filed: Sep. 29, 2020

(65) Prior Publication Data

US 2021/0008549 A1 Jan. 14, 2021

Related U.S. Application Data

(63) Continuation of application No. 15/324,122, filed as application No. PCT/US2015/039695 on Jul. 9, 2015, now Pat. No. 10,814,322.

(60) Provisional application No. 62/022,376, filed on Jul. 9, 2014.

(51) Int. Cl.
*B01L 3/00* (2006.01)
*G01N 33/487* (2006.01)

(52) U.S. Cl.
CPC ....... *B01L 3/502707* (2013.01); *B01L 3/5027* (2013.01); *G01N 33/48707* (2013.01); *B01L 2300/0645* (2013.01); *B01L 2300/088* (2013.01); *B01L 2300/0816* (2013.01); *B01L 2300/0887* (2013.01)

(58) Field of Classification Search
CPC ............. B01L 3/5027; B01L 3/502707; B01L 2300/0645; B01L 2300/0816; B01L 2300/088; B01L 2300/0887; G01N 33/48707
See application file for complete search history.

(56) References Cited

U.S. PATENT DOCUMENTS

| | | |
|---|---|---|
| 6,258,229 B1 | 7/2001 | Winarta et al. |
| 7,332,902 B1 | 2/2008 | Vermeire et al. |
| 7,824,529 B2 | 11/2010 | Lauks |
| 8,506,778 B2 | 8/2013 | Lauks et al. |
| 8,728,288 B2 | 5/2014 | Aas et al. |
| 2008/0233011 A1 | 9/2008 | Gundel et al. |
| 2009/0032401 A1 | 2/2009 | Ronaghi |
| 2010/0301398 A1 | 12/2010 | Rothberg et al. |
| 2011/0203941 A1 | 8/2011 | Say |

(Continued)

FOREIGN PATENT DOCUMENTS

| | | |
|---|---|---|
| JP | 2001516025 A | 9/2001 |
| JP | 2006504974 A | 2/2006 |

(Continued)

OTHER PUBLICATIONS

Choi, Kyungyong, et al. "Integration of field effect transistor-based biosensors with a digital microfluidic device for a ab-on-a-chip application." Lab on a Chip 12.8 (2012): 1533-1539.

(Continued)

*Primary Examiner* — Robert J Eom

(57) ABSTRACT

In one aspect, the inventive concepts disclosed herein are directed to a sensor assembly which contains a first planar substrate and a second planar substrate which respectively support opposing sensor arrays and contains an integrated flow path extending between the first and second substrates.

11 Claims, 9 Drawing Sheets

(56) References Cited

U.S. PATENT DOCUMENTS

| | | |
|---|---|---|
| 2012/0135509 A1 | 5/2012 | Hall |
| 2013/0189158 A1 | 7/2013 | Li et al. |
| 2014/0124382 A1 | 5/2014 | Edelbrock et al. |

FOREIGN PATENT DOCUMENTS

| | | |
|---|---|---|
| JP | 2007511740 A | 5/2007 |
| JP | 2008082961 A | 4/2008 |
| JP | 2010522321 A | 7/2010 |
| WO | 2013065994 A1 | 5/2013 |

OTHER PUBLICATIONS

European Search Report and Written Opinion of European Application No. 15818776.5 dated Jun. 29, 2017.
International Search Report and Written Opinion of International Application No. PCT/US2015/039695 dated Oct. 1, 2015.

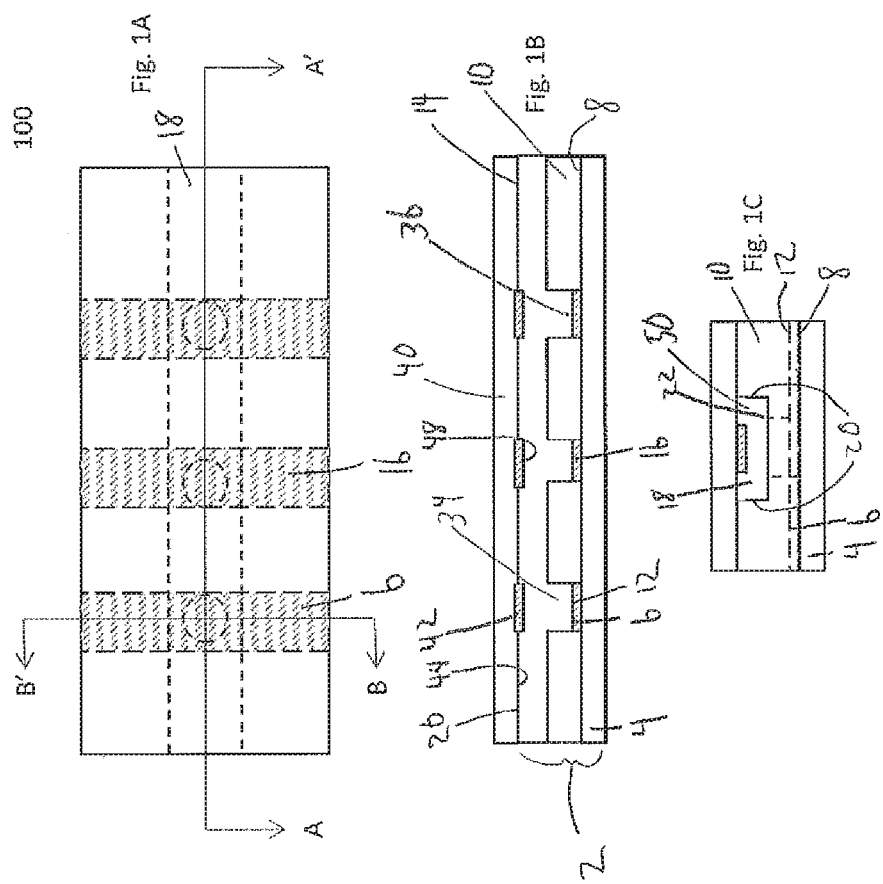

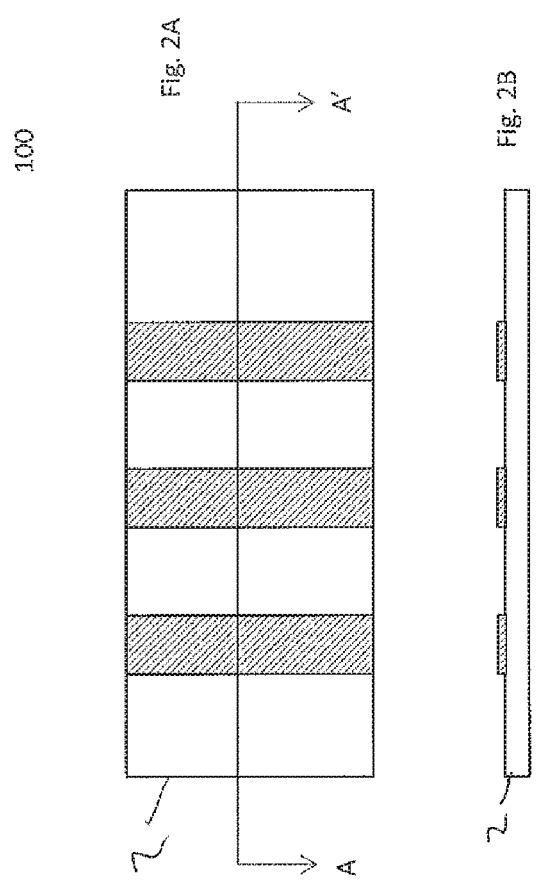

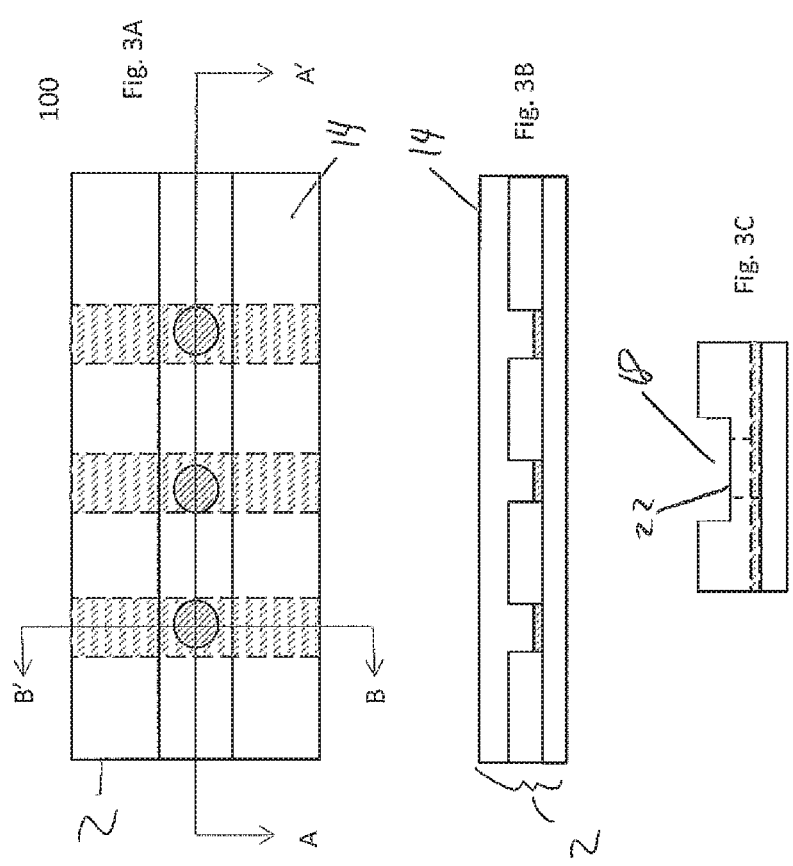

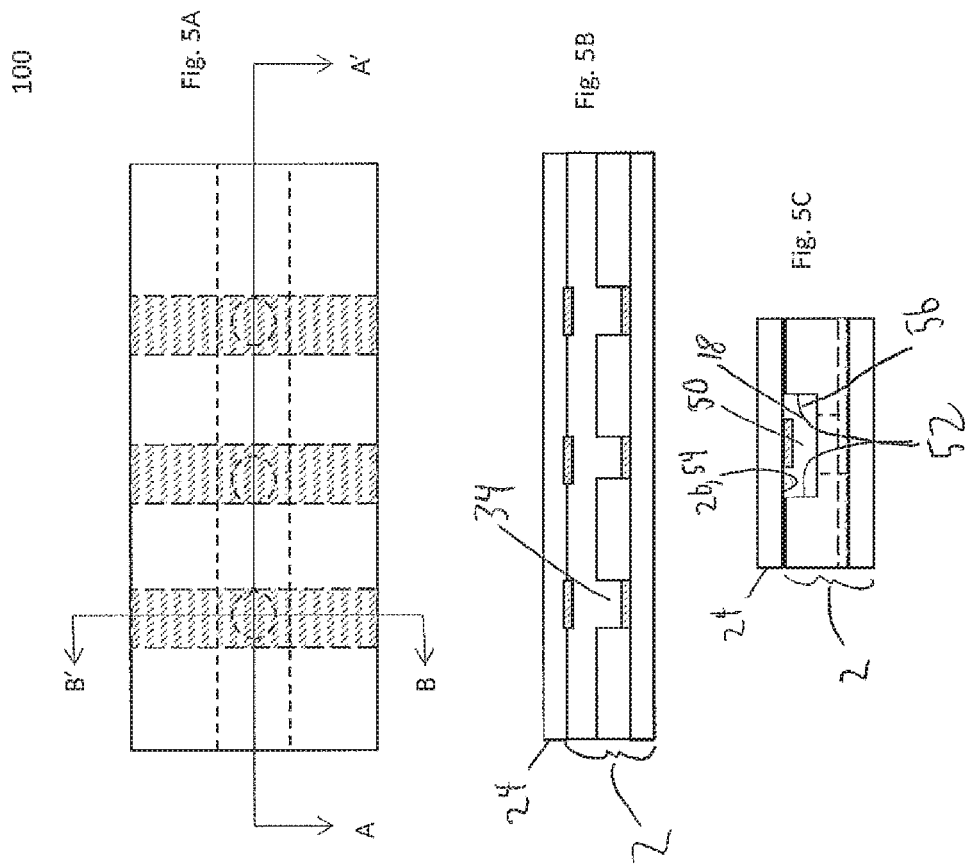

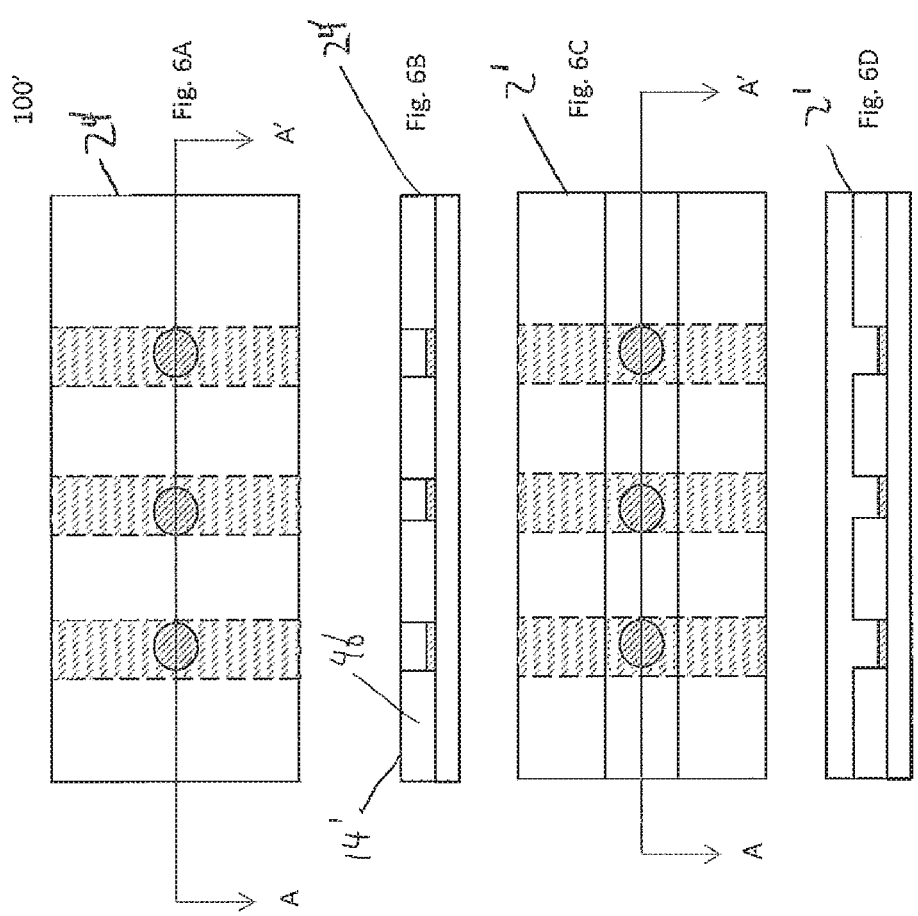

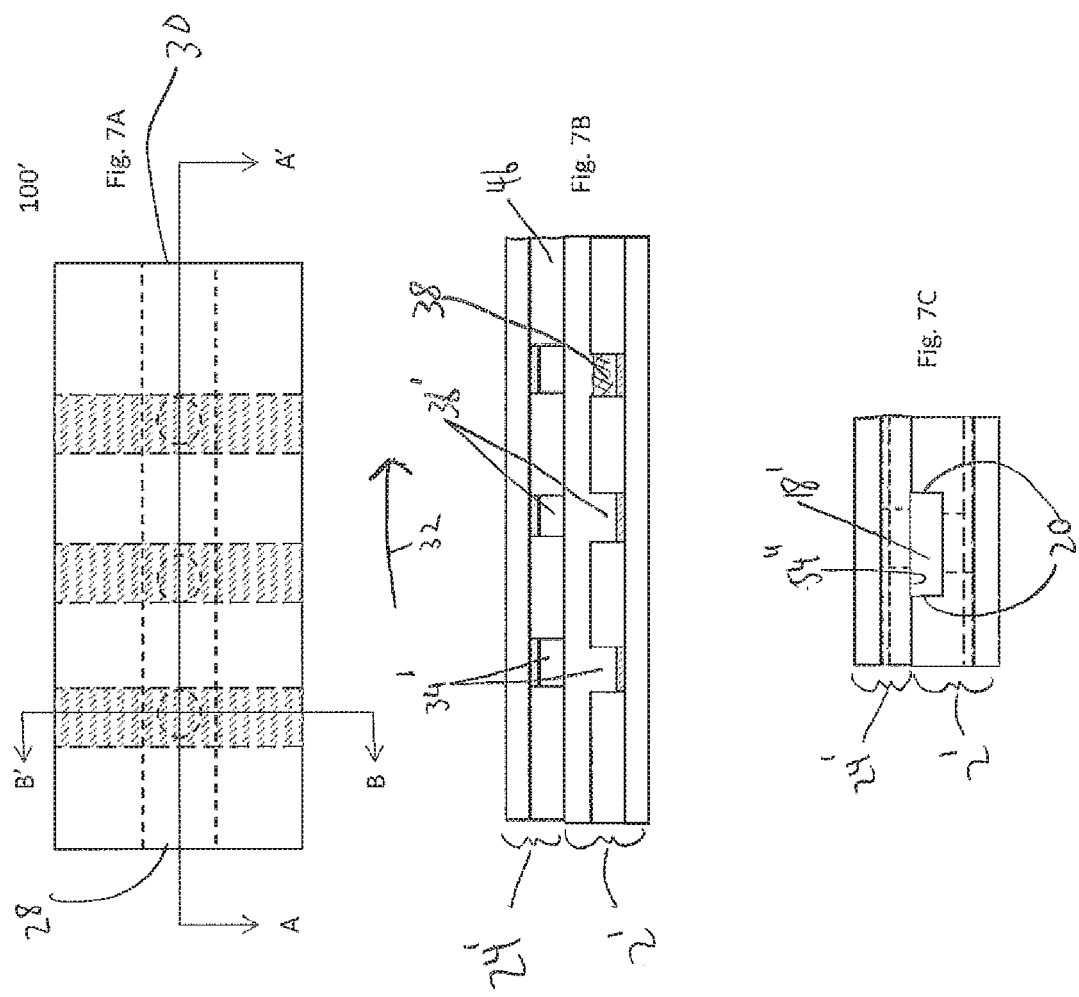

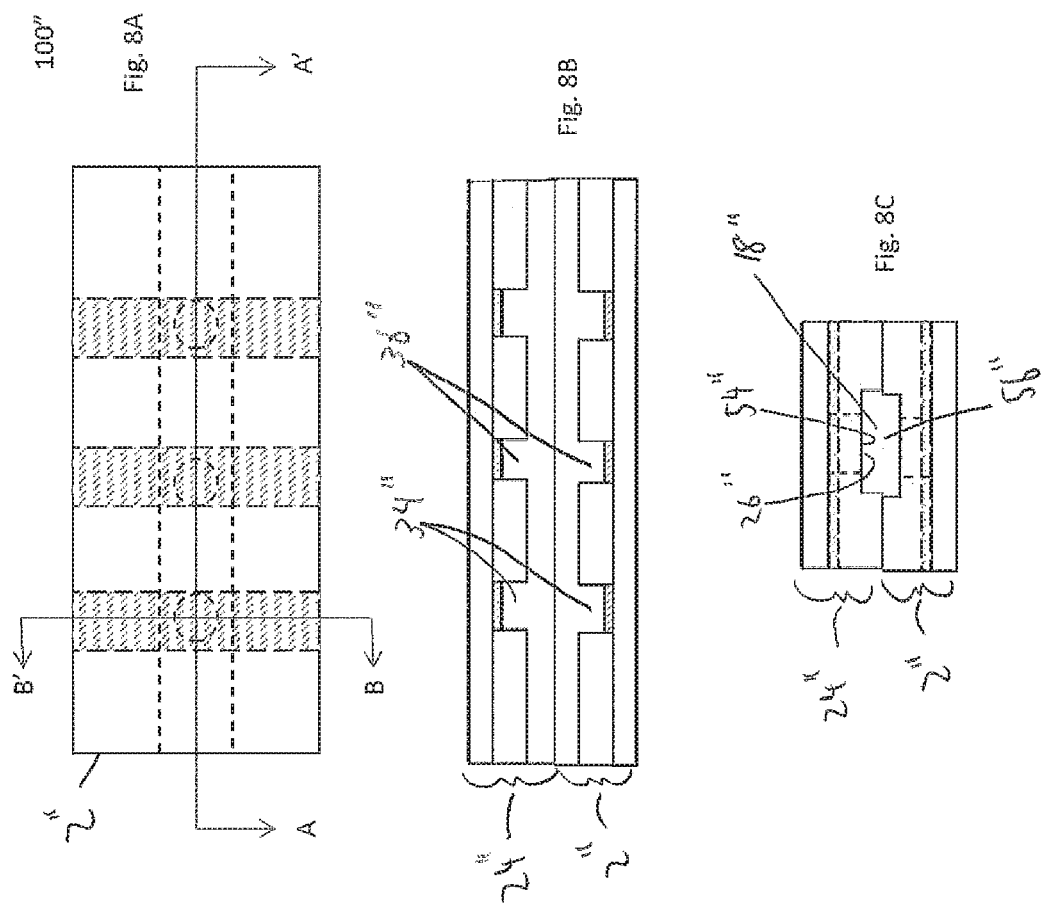

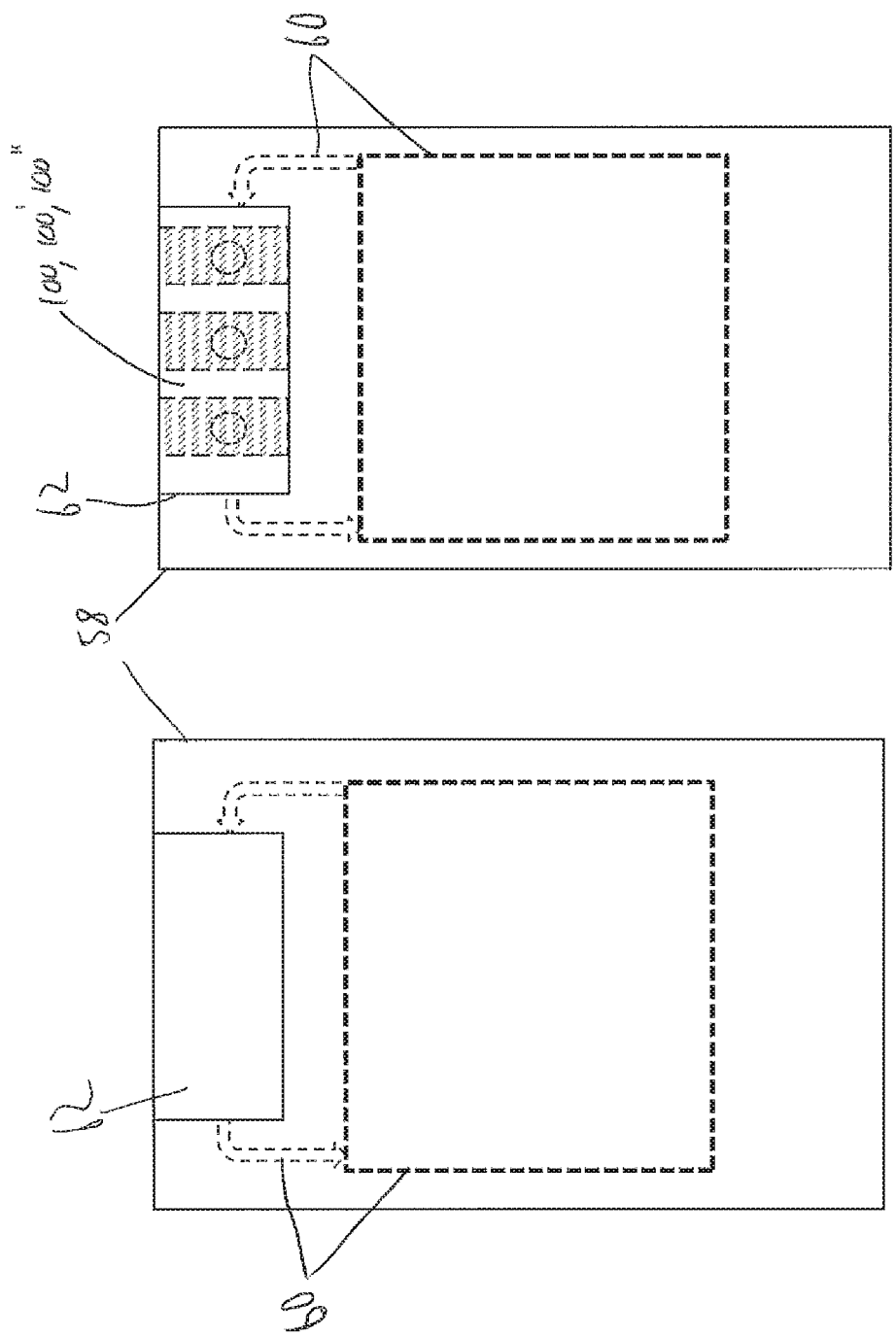

LOW SAMPLE VOLUME SENSING DEVICE

The subject application is a continuation of U.S. Ser. No. 15/324,122, filed Jan. 5, 2017; which is a US national stage application under 35 USC § 371 of International Application No. PCT/US2015/039695, filed Jul. 9, 2015; which claims priority under 35 USC § 119(e) to US Provisional Application No. 62/022,376, filed Jul. 9, 2014. The entirety of each of the above-referenced patents and patent applications are hereby expressly incorporated herein by reference.

BACKGROUND

This disclosure relates to a sensing device which allows for multiple tests to be run concurrently using a small sample volume.

SUMMARY OF THE INVENTIVE CONCEPT(S)

In one aspect, the inventive concepts disclosed herein are directed to a sensor assembly which contains a first and a second planar substrate. The first planar substrate having a base layer, a conductive layer formed on a first planar surface of the base layer, and an dielectric layer formed on at least one of a first planar surface of the conductive layer or the first planar surface of the base layer, the dielectric layer having a first planar surface located a distance from the first planar surface of the conductive layer. The conductive layer comprising at least at least a first electrical contact and a second electrical contact electrically isolated from the first electrical contact. The dielectric layer defining a liquid flow path through the dielectric layer, the flow path having two side walls and a bottom surface extending between the two side walls, the two side walls extending between the first planar surface of the base layer and the first planar surface of the dielectric layer. The dielectric layer further defining a first sensing area and a second sensing area above the respective first electrical contact and the second electrical contact of the conductive layer, the first sensing area and the second sensing area allowing liquid in the flow path to contact the first electrical contact and the second electrical contact, respectively. The second planar substrate being bonded to the first substrate, when bonded to the first substrate the second substrate defining a upper surface of the liquid flow path, the upper surface of the liquid flow path extending between the two side walls and located at a distance from the bottom surface of the flow path.

BRIEF DESCRIPTIONS OF THE DRAWINGS

FIGS. 1A to 1C illustrate one embodiment of a sensor assembly.

FIGS. 2A to 5C depict an illustrative method of manufacturing the sensor assembly.

FIGS. 6A to 7C illustrate an alternative embodiment of the sensor assembly.

FIGS. 8A to 8C illustrate yet another alternative embodiment of the sensor assembly.

FIGS. 9A to 9B illustrate incorporating the sensory assembly into a fluidic housing.

DETAILED DESCRIPTION OF THE INVENTIVE CONCEPT(S)

Figure 4A:
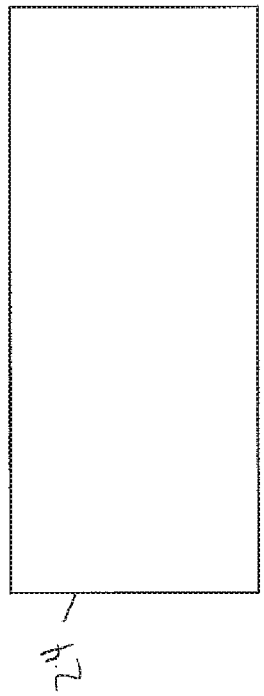

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts within the instant disclosure may be practiced without these specific details. In other instances, well-known features have not been described in detail to avoid unnecessarily complicating the instant disclosure.

As used herein, the terms "comprises," "comprising," "includes," "including," "has," "having" or any other variation thereof, are intended to cover a non-exclusive inclusion. For example, a composition, a process, method, article, or apparatus that comprises a list of elements is not necessarily limited to only those elements but may include other elements not expressly listed or inherently present therein.

As used herein the terms "approximately," "about," "substantially" and variations thereof are intended to include not only the exact value qualified by the term, but to also include some slight deviations therefrom, such as deviations caused by measuring error, manufacturing tolerances, wear and tear on components or structures, settling or precipitation of cells or particles out of suspension or solution, chemical or biological degradation of solutions over time, stress exerted on structures, and combinations thereof, for example.

As used herein, the term "sample" and variations thereof is intended to include biological tissues, biological fluids, chemical fluids, chemical substances, suspensions, solutions, slurries, mixtures, agglomerations, tinctures, slides, powders, or other preparations of biological tissues or fluids, synthetic analogs to biological tissues or fluids, bacterial cells (prokaryotic or eukaryotic), viruses, single-celled organisms, lysed biological cells, fixed biological cells, fixed biological tissues, cell cultures, tissue cultures, genetically engineered cells and tissues, genetically engineered organisms, and combinations thereof, for example.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present). An inclusive or may be understood as being the equivalent to: at least one of condition A or B.

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Figure 4B:
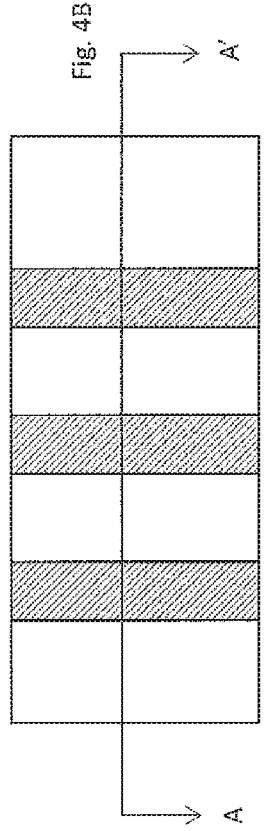
Figure 4C:
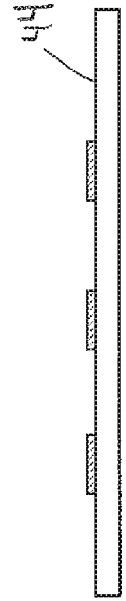

The inventive concepts disclosed herein are generally directed to the need to minimize the sample volume required to test two or more analytes concurrently. Low sample volumes are desirable when the sample is limited, such as in the case of neonatal patients, or when the sample itself is expensive. As opposed to prior art configurations, which required the volume to increase with the number of analytes being detected, the required sample volume can be greatly reduced when the sensors are arranged in such a way that they are facing one another in a sandwich configuration (also referred to as an opposing sensor array) rather than in a coplanar configuration. Illustrative opposing sensor arrays are discussed in connection with FIGS. 1A to 8B below.

FIGS. 1A-1C depict an embodiment of a sensor assembly 100. FIGS. 1B and 1C depict a view of sensor assembly 100 along lines A-A' and B-B', respectively. Sensor assembly 100 contains a first planar substrate 2 having a base layer 4, and a conductive layer 6 formed on a first planar surface 8 of the base layer 4. Base layer 4 may be made from, for example, ceramic, polymer, foil, or any other type of material known to someone of ordinary skill in the art. Conductive layer 6 contains at least at least two electrically isolated electrical contacts 16 made, for example, using a thick film approach (e.g., screen printing, rotogravure, pad printing, stenciling conductive material such as carbon, Cu, Pt, Pd, Au, and/or Nanotubes, etc. . . . ) or a thin firm approach (e.g., by sputtering, thermal spraying, and/or cold spraying conductive material). While the electrical contacts 16 in FIG. 1 are depicted as being rectangular, it should be understood that this is an exemplary configuration only.

First planar substrate 2 of FIGS. 1A-1C further contains one or more dielectric layers 10 formed on one or both of the first planar surface 12 of the conductive layer 6 or the first planar surface 8 of the base layer 4. The dielectric layer 10 has a first planar surface 14 located a distance from the first planar surface 12 of the conductive layer 6. The dielectric layer 10 may be any type of insulating layer or inert layer. For example, in an embodiment, dielectric layer 10 may be a DTE insulating layer (such as a thick film dielectric or polymer/non-conductive film).

The dielectric layer(s) 10 define a liquid flow path 18 integrated into the dielectric layer(s) 10. The flow path 18 has two side walls 20 and a bottom surface 22 extending between the two side walls 20. The two side walls 20 extend between the first planar surface 8 of the base layer 4 and the first planar surface 14 of the dielectric layer 10.

The dielectric layer(s) 10 also includes sensing areas 34 located within the liquid flow path 18 above one or more of the electrical contacts 16 located in the liquid flow path 18. Each sensing area 34 allows liquid in the flow path 18 to come into contact with the electrical contacts 16. As depicted in FIG. 1, sensing areas 34 may include reaction wells 36 formed in the dielectric layer(s) 10 in the bottom surface 22 of the liquid flow path 18. These reaction wells 36 may be partially or completely filled with reagents 38 which, in cooperation with the electrical contacts 16, comprise a sensor. Sensing area 34 may refer to the area above a reaction well 36 as well as area inside of the reaction well not occupied by the electrical contact or the reagents 38. Where, for example, the electrical contacts 16 are substantially flush with the bottom surface 22 of the liquid flow path 18 or extend a distance above the first planar surface of the base layer 4, sensing area 34 refers to the area directly above each electrical contact 16. As depicted in FIG. 1, the flow path 18 in dielectric layer(s) 10 may take the form of a trough 40 through which the liquid sample flows in the direction of fluid travel 32. The reaction wells 36 may be located in the bottom of the trough 40

Sensor assembly 100 further contains a second planar substrate 24 bonded to the first substrate 2. The second planar substrate 24 contains a second base layer 40. The second planar substrate 24 may also contain a second conductive layer 42 formed on a first planar surface 44 of the base layer 40. The second planar substrate 24 may further contain one or more dielectric layers 46 formed on at least one of the first planar surface 48 of the conductive layer 42 or the first planar surface 44 of the base layer 40. Base layer 40, conductive layer 42, and dielectric layer(s) 46 may be formed in a manner similar to that of base layer 4, conductive layer 6, and dielectric layer (s) 10, respectively. For example, the second planar substrate 24 shown in FIG. 1 contains only the planar base layer 40 and the planar conductive layer 42 disposed thereon.

When bonded to the first substrate 2, the second substrate 24 depicted in FIG. 1 defines an upper surface 26 of the liquid flow path 18, the upper surface 26 of the liquid flow path 18 extending between the two side walls 20 and located at a distance from the bottom surface 22 of the flow path 18. The liquid flow path 18 also has an inlet 28 and an outlet 30. A liquid sample flows in through the inlet 28 and out through the outlet 30 in the direction of fluid travel (arrow 32). As will be appreciate by a person skilled in the art, inlet 28 and/or outlet 30 may be formed in a variety of ways. For example, inlet 28 and/or outlet 30 may be openings in the side of the device (for example, as is depicted in FIGS. 1A-1C) or may be ports (e.g., apertures) formed in one or more layers of substrates 2 and 24.

In other embodiments, second planar substrate 24 may also have one or more dielectric layers 46. Such is the case with the two embodiments of sensor assembly 100' and 100" which are depicted in FIGS. 6A to 7C and FIGS. 8A-8C, respectively. In FIGS. 8A-8C, the second planar substrate 24 contains similar features to that of substrate 2—such as an integrated flow path 50 defined by side walls 52 and a top surface 54. In such a configuration, both substrates 2 and 24 contain integrated flow paths 18 and 50, respectively. When bonded to the first substrate 2, the first substrate 2 and the second substrate 24 formed a flow path 56 (which may also be referred to as a flow through channel) in which the respective flow paths 18 and 50 at least partially align with one another. Similarly, in the embodiment depicted in FIG. 6A-7C, the second planar substrate 24 contains similar somewhat features to that of substrate 2—such as reaction wells 36 but not a flow path 50. It should be understood that the second substrate 24 can be formed in a manner similar to that of substrate 2.

Planar substrates 2 and 24 may be bonded to one another via a variety of methods. Such methods include: using adhesive, pressure sensitive adhesive, UV adhesive, thermal adhesives, Ultrasonic welding, or thermally tacking dielectric layers together. Alternatively, or additionally, substrates 2 and 24 may be bonded together using a tongue and groove configuration.

FIGS. 2A through 5C depict an illustrative method of manufacturing the sensor assembly 100. FIGS. 2A to 3C depict the formation of the first planar substrate 2. FIGS. 4A to 4C depict the formation of the second planar substrate 24. FIGS. 5A to 5C depict the second planar substrate 24 positioned above the first planar substrate 2.

FIGS. 6A to 6D depict an illustrative method of manufacturing the sensor assembly 100'. FIGS. 6A to 6B depict the formation of the first planar substrate 2'. FIGS. 6C to 6D depict the formation of the second planar substrate 24'.

FIGS. 7A to 7C depict the second planar substrate 24' positioned above the first planar substrate 2'.

FIGS. 9A and 9B depict an embodiment where sensory assembly 100, 100' or 100" is incorporated into a fluidic housing 58. Housing 58 may be made of molded plastic and/or polymer and have microfluidic and/or macrofluidic channels 60 incorporated therein (represented by the dashed arrows/box). The sensory assembly 100, 100' or 100" can then be inserted into an opening 62 into the housing 58 such that the liquid flow path(s) 18, 50, and/or 56 are placed in fluidic contact with the microfluidic and/or macrofluidic channels 60 such that liquid flows through from the channels 60 into the sensory assembly 100, 100' or 100" and back into the channels 60 in the direction of the liquid flow path 18.

Sensory assembly 100, 100' or 100" can be bonded to housing 58 via, for example, adhesive, ultrasonic welding, thermal sealing, and solvent bonding, etc.

The following is a non-limiting list of illustrative embodiments based on the above description.

1. A sensor assembly comprising: a first planar substrate having a base layer, a conductive layer formed on a first planar surface of the base layer, and an dielectric layer formed on at least one of a first planar surface of the conductive layer or the first planar surface of the base layer, the dielectric layer having a first planar surface located a distance from the first planar surface of the conductive layer, the conductive layer comprising at least at least a first electrical contact and a second electrical contact electrically isolated from the first electrical contact, the dielectric layer defining a liquid flow path through the dielectric layer, the flow path having two side walls and a bottom surface extending between the two side walls, the two side walls extending between the first planar surface of the base layer and the first planar surface of the dielectric layer, and the dielectric layer further defining a first sensing area and a second sensing area above the respective first electrical contact and the second electrical contact of the conductive layer, the first sensing area and the second sensing area allowing liquid in the flow path to contact the first electrical contact and the second electrical contact, respectively; and a second planar substrate, the second substrate being bonded to the first substrate, when bonded to the first substrate the second substrate defining a upper surface of the liquid flow path, the upper surface of the liquid flow path extending between the two side walls and located at a distance from the bottom surface of the flow path.
2. The device of illustrative embodiment 1, wherein the dielectric layer comprises a first and a second planar layer, the first dielectric layer is formed on formed on the first planar surface of the conductive layer and defines the first and the second sensor areas, the second dielectric layer being formed on the first dielectric layer and defines the flow path.
3. The device of illustrative embodiments 1 or 2, wherein the first and the second sensor areas comprise wells at least one of which contains a substance which aids in the detection of a substance in a liquid in the flow path.
4. The device as in any one of illustrative embodiment 1, 2, or 3, wherein the second substrate comprises a first planar substrate having a base layer, a conductive layer formed on a first planar surface of the base layer, and an dielectric layer formed on first planar surface of the conductive layer, the dielectric layer having a first planar surface located a distance from the first planar surface of the conductive layer, wherein the conductive layer comprising at least at least a first electrical contact and a second electrical contact electrically isolated from the first electrical contact, the first and the second electrical contacts of the second substrate corresponding to the respective first and the second electrical contacts of the first substrate.
5. The device as illustrative embodiment 4, wherein the dielectric layer defining a liquid flow path through the dielectric layer, the flow path having two side walls and a bottom surface extending between the two side walls, the two side walls extending between the first planar substrate of the base layer and the first planar surface of the dielectric layer, when bonded to the first substrate the flow path of the second substrate defining an upper portion of a combined flow path in which the bottom surface of the first substrate faces the bottom surface of the second substrate, and wherein the dielectric layer further defining a first sensing area and a second sensing area above the respective first electrical contact and the second electrical contact of the conductive layer, the first sensing area and the second sensing area allowing liquid in the flow path to contact the first electrical contact and the second electrical contact, respectively.
6. The device as in any one of illustrative embodiment 1, 2, 3, 4, or 5 wherein the first substrate and the second substrate are bonded to one another using one or more of: a tongue and grove configuration, an adhesive, thermal tacking, or ultrasonic welding.
7. A fluidic housing comprising the sensor assembly as in any one of illustrative embodiments 1, 2, 3, 4, 5, or 6.

What is claimed is:

1. A sensor array for concurrently testing a first analyte and a second analyte, comprising:
   an inlet;
   an outlet;
   a flow path configured to provide fluid from the inlet to the outlet, the flow path having a first sensing area to test the first analyte and a second sensing area to test the second analyte, the flow path defined by:
   a first dielectric layer positioned on a first conductive layer, the first conductive layer having a first electrical contact electrically isolated from a second electrical contact such that the first sensing area is positioned adjacent to the first electrical contact and the second sensing area is positioned adjacent to the second electrical contact; and,
   a second dielectric layer positioned on a second conductive layer, the second conductive layer having a third electrical contact positioned in an opposing orientation relative to the first electrical contact and a fourth electrical contact positioned in an opposing orientation relative to the second electrical contact such that the flow path passes between the first and third electrical contacts, and between the second and fourth electrical contacts;
   wherein the flow path is configured to allow fluid to contact conductive material of the first electrical contact of the first sensing area and the second electrical contact second sensing area.
2. The sensor array of claim 1, wherein the first sensing area defines a first well configured to allow liquid in the flow path to contact conductive material of the first electrical contact.

3. The sensor array of claim 2, wherein the second sensing area defines a second well configured to allow liquid in the flow path to contact conductive material of the second electrical contact.

4. The sensor array of claim 1, wherein the first sensing area includes a first reaction well formed in the first dielectric layer.

5. The sensor array of claim 4, wherein at least a portion of the first reaction well includes a first reagent.

6. The sensor array of claim 5, wherein the second sensing area includes a second reaction well formed in the first dielectric layer.

7. The sensor array of claim 6, wherein at least a portion of the second reaction well includes a second reagent.

8. The sensor array of claim 6, wherein the flow path in the first dielectric layer forms a trough with the first reaction well and the second reaction well positioned at a bottom of the trough.

9. The sensor array of claim 1, wherein the flow path is an integrated flow path having a first flow path and a second flow path, the first flow path and the second flow path configured to be at least partially aligned.

10. The sensor array of claim 1, wherein the first sensing area includes a first reaction well formed in the first dielectric layer and the second dielectric layer defines a second reaction well formed in the second dielectric layer and configured to be positioned above the first reaction well.

11. The sensor array of claim 10, wherein the flow path is an integrated flow path having a first flow path and a second flow path, the first flow path configured to provide fluid to the first reaction well and the second flow path configured to provide fluid to the second reaction well.

* * * * *